(12) United States Patent
Passerini et al.

(10) Patent No.: US 10,758,200 B2
(45) Date of Patent: Sep. 1, 2020

(54) METHOD AND SYSTEM FOR ASSESSING A HAEMODYNAMIC PARAMETER

(71) Applicant: Siemens Healthcare GmbH, Erlangen (DE)

(72) Inventors: Tiziano Passerini, Plainsboro, NJ (US); Lucian Mihai Itu, Brasov (RO); Thomas Redel, Poxdorf (DE); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 93 days.

(21) Appl. No.: 16/198,566

(22) Filed: Nov. 21, 2018

(65) Prior Publication Data
US 2019/0150869 A1    May 23, 2019

(30) Foreign Application Priority Data

Nov. 22, 2017    (EP) .................... 17464012

(51) Int. Cl.
*A61B 6/00* (2006.01)
*G06N 3/08* (2006.01)
(Continued)

(52) U.S. Cl.
CPC ............ *A61B 6/5217* (2013.01); *A61B 6/481* (2013.01); *A61B 6/504* (2013.01); *A61B 6/507* (2013.01);
(Continued)

(58) Field of Classification Search
CPC ....... A61B 6/5217; A61B 6/481; A61B 6/504; A61B 6/507; A61B 6/5229; G16H 30/20;
(Continued)

(56) References Cited

U.S. PATENT DOCUMENTS

| 9,087,147 B1* | 7/2015 | Fonte ..................... A61B 6/503 |
| 2005/0043614 A1* | 2/2005 | Huizenga ................ C23F 11/08 |
| | | 600/427 |

(Continued)

FOREIGN PATENT DOCUMENTS

| EP | 3218872 A2 | 9/2017 |
| WO | WO2016075331 A3 | 8/2016 |

OTHER PUBLICATIONS

Bullitt, E., A. Liu, and S. M. Pizer. "Three-dimensional reconstruction of curves from pairs of projection views in the presence of error. I. Algorithms." Medical Physics 24.11 (1997): 1671-1678.
(Continued)

*Primary Examiner* — Pakee Fang
(74) *Attorney, Agent, or Firm* — Lempia Summerfield Katz LLC (57) ABSTRACT

A method and a corresponding system for assessing a haemodynamic parameter for a vascular region of interest of a patient based on angiographic images are provided. After acquiring multiple angiographic images, a three dimensional (3D) representation of at least a first portion of the respective region of interest is performed, and geometric features are extracted from complete or partial views. Additional geometric features are extracted from partial incomplete views. A complete set of 3D geometric features for an anatomical structure, such as a vessel tree, is then generated by combining the extracted geometric features and estimating any missing geometric features. Using the complete set of 3D geometric features, a feature-based assessment of the haemodynamic parameter, such as a fractional flow reserve, is then performed.

20 Claims, 3 Drawing Sheets

(51) Int. Cl.
*G16H 30/20* (2018.01)
*G06N 20/00* (2019.01)
*G06T 7/00* (2017.01)

(52) U.S. Cl.
CPC .............. *A61B 6/5229* (2013.01); *G06N 3/08* (2013.01); *G06N 20/00* (2019.01); *G06T 7/0012* (2013.01); *G16H 30/20* (2018.01); *G06T 2207/10021* (2013.01); *G06T 2207/10116* (2013.01); *G06T 2207/30104* (2013.01)

(58) Field of Classification Search
CPC ........ G06N 20/00; G06N 3/08; G06T 7/0012; G06T 2207/10021; G06T 2207/10116; G06T 2207/30104
See application file for complete search history.

(56) References Cited

U.S. PATENT DOCUMENTS

| | | | |
|---|---|---|---|
| 2010/0220916 A1* | 9/2010 | Salafia | G06T 7/0012 382/134 |
| 2011/0081059 A1* | 4/2011 | Salafia | G06T 7/0012 382/128 |
| 2013/0132054 A1 | 5/2013 | Sharma | |
| 2014/0058715 A1 | 2/2014 | Sharma et al. | |
| 2015/0065846 A1* | 3/2015 | Choi | G06T 7/0012 600/407 |
| 2016/0148371 A1 | 5/2016 | Itu et al. | |
| 2016/0148372 A1 | 5/2016 | Itu et al. | |
| 2017/0032097 A1 | 2/2017 | Itu et al. | |
| 2017/0095292 A1* | 4/2017 | Taylor | A61B 34/10 |
| 2017/0245821 A1 | 8/2017 | Itu et al. | |
| 2018/0116725 A1* | 5/2018 | Ashikaga | A61B 34/10 |

OTHER PUBLICATIONS

European Office Action for European Patent Application No. 174640112.8—1210 dated May 17, 2018.

Sharma, Puneet, et al. "A framework for personalization of coronary flow computations during rest and hyperemia." Engineering in Medicine and Biology Society (EMBC), 2012 Annual International Conference of the IEEE. IEEE, 2012. p. 6665-6668.

* cited by examiner

METHOD AND SYSTEM FOR ASSESSING A HAEMODYNAMIC PARAMETER

This application claims the benefit of EP17464012, filed on Nov. 22, 2017, which is hereby incorporated by reference in its entirety.

BACKGROUND

The present embodiments relate to assessing a haemodynamic parameter.

Today, angiography is a well-established medical imaging technique. Coronary angiography, for example, is considered the gold standard for anatomical assessment of coronary artery disease. Nonetheless, coronary angiography has some intrinsic limitations and shortcomings. One of the most significant limitations of coronary angiography is an inability to accurately assess the physiological significance of lesions. Subject-specific physiology modeling may address this limitation. The approach includes determining the geometry features of the patient-specific arterial tree, and subsequent use of a computational model designed to predict functional diagnostic indices, such as FFR, as a function of the geometry.

US 2014/0058715A1 discloses a method and a system for non-invasive functional assessment of a coronary artery stenosis. Therein, patient-specific anatomical measurements of coronary arteries are extracted from medical image data acquired during a rest state of the patient. Based thereon, patient-specific rest state boundary conditions of a model of coronary circulation are calculated. Additionally, patient-specific hyperemic boundary conditions of the model are calculated based on the rest boundary conditions and a model for simulated hyperaemia. A hyperemic blood flow and pressure across a stenosis region are then simulated using the model of coronary circulation and the hyperemic boundary conditions to, finally, calculate a fractional flow reserve of the stenosis region.

US 2017/0032097A1 discloses a method and a system for enhancing medical image-based blood flow computations using invasively acquired physiological measurements. A patient-specific anatomical model of the patient's vessels is generated from non-invasively acquired medical image data. A computational blood flow model is then personalized using the invasive physiological measurements. One or more haemodynamic quantities of interest are then computed using this personalized computational blood flow model.

In standard coronary angiography, a limited number of 2D projections of vessels or vessel segments of interest are acquired, for example, through x-ray imaging. A combination of a pair of 2D images or views of the same vessel taken from different angles or angulations generally allows or enables a representation of the vessel in 3D space. The representation in 3D space may include or consist of a 3D anatomically accurate geometrical model, to which the following description may generically refer as a 3D reconstruction. Nonetheless, a 3D representation of, for example, a vascular tree may include or consist of, for example, a tree of branching centerlines of vessels or vessel segments, with each centerline point being associated to a radius or diameter value representing a local size of the respective vessel or vessel segment. Equivalently, within the scope of the present embodiments, the vascular tree of interest may be represented by a collection of features of a 3D geometry, such as a number of branches, a length of each branch, an average caliber of the branch, a shape of a cross-section of each branch, etc.

Since coronary angiography is typically concerned with and therefore focused on very specific parts or features, such as a stenosis, a respective field of view in each 2D image or 2D projection is optimized for visualization of this exact part or feature of the diseased vessel. In many cases, this limits the possibility of reconstructing or characterizing neighboring vessels to obtain a complete representation or reconstruction or model of the vessel tree surrounding an imaged feature of interest, such as a stenosis. In typical sets of angiographic images, the neighboring, presumably healthy, vessels may not be clearly visible, for example, due to a complex geometry of the vessel tree and/or foreshortening or overlaps with other anatomical structures. In these cases or conditions, it is not possible to fully represent or reconstruct the complete 3D geometry and topology of the vessel tree or arterial tree.

In some cases, additional images, such as previously acquired anatomical scans of the same patient, may provide additional data to enable the 3D representation of the complete vessel tree. If there is sufficient overlap between the angiographic images and the additional images or data, a single comprehensive 3D representation may be achieved by combining all available data. The required additional data is, however, not reliably available for every patient. Therefore, to fully represent or reconstruct the vessel tree in a region of interest, additional images would have to be acquired at the cost of additional exposure of the patient to radiation and contrast medium as well as additional expenditure of time and money.

Even if additional images are available or acquired, it may be impossible or extremely difficult to combine all data into a single complete and correct 3D representation. One difficulty lies in the needed registration between different datasets, which, for example, may have been acquired at different points in time and/or using different imaging equipment. If, for example, the patient has been moved or repositioned between the respective acquisitions of the different datasets, corresponding representations may be obtained in different coordinate systems. In this case, combining the respective data or models into a single cohesive and consistent 3D model may, at least for practical purposes, be impossible without proper position tracking at all times.

SUMMARY AND DESCRIPTION

The scope of the present invention is defined solely by the appended claims and is not affected to any degree by the statements within this summary.

The present embodiments may obviate one or more of the drawbacks or limitations in the related art. For example, functional assessment of a vessel condition even in cases where the available data is insufficient for representing or reconstructing a complete 3D model of the surrounding vessel when using conventional reconstruction algorithms is provided.

A method according to one or more of the present embodiments is concerned with assessing a haemodynamic parameter for a vascular region of interest of a patient based on angiographic images. The method includes acquiring multiple angiographic images of the region of interest with the angiographic images showing at least a first portion of the region of interest from at least two different angles or angulations to allow for a 3D reconstruction of the first portion. The 3D reconstruction (e.g., a 3D model) of at least the first portion of the region of interest is then generated from the angiographic images. The method further includes extracting 3D geometric features of the first portion from the 3D reconstruction.

Geometric features in terms of the present embodiments may, for example, be a diameter or radius and/or a shape and/or an orientation of a vessel, a length of a segment of a vessel, and/or a size and/or shape of a stenosis of the vessel, or the like.

Oftentimes, a set of angiographic images does not provide sufficient data to completely or fully three-dimensionally represent an anatomy or anatomic structure (e.g., a vessel tree) in the region of interest. The region of interest is an area or volume of the patient that is not limited to a location of a stenosis or immediate surroundings but may be significantly larger. The region of interest may, for example, include multiple bifurcations and/or branches of vessels (e.g., a vessel tree). The region of interest may also span or include multiple stenoses, which may be located in different segments of a vessel, in different branches of the vessel tree, or even in different vessels altogether. For an accurate assessment of the haemodynamic parameter, a complete characterization or understanding of not only a particular stenosis or immediate surroundings but of the whole region of interest may be required.

To avoid the need for acquiring further images in addition to the acquired set of angiographic images used for picturing one or more stenoses, the method according to one or more of the present embodiments includes further acts. As part of the method, at least one additional geometric feature for at least a second portion of the region of interest is extracted from the angiographic images. The second portion may be characterized in that the angiographic images contain insufficient data about the second portion to allow for a complete 3D representation using conventional (e.g., well-known) algorithms. The second portion may, for example, be located next to a segment of a vessel containing a stenosis, and/or the second portion may be located between two stenoses in different parts of the region of interest. The first portion and/or the second portion of the region of interest may each be one single connected part of the region of interest. Alternatively, the first portion and/or the second portion may consist of or include multiple unconnected parts, areas, or sub-regions of the region of interest.

In a further act of the presently described method, a complete set of 3D geometric features for the region of interest is generated. This is done by combining or stitching together the extracted 3D geometric features and the at least one additional geometric feature. Any missing 3D geometric features are estimated from the extracted geometric features (e.g., from the 3D geometric features and/or the at least one additional geometric feature) and/or from the angiographic images based on a predefined ruleset. In other words, suitable assumptions, extrapolations, interpolations, and/or continuations, or the like may be made regarding the missing 3D geometric features or any corresponding missing information to generate or acquire a complete 3D geometric characterization or description of the region of interest or at least of a vessel tree that extends in or throughout the region of interest. The missing 3D geometric features are geometric features of the second portion, providing that the missing 3D geometric features may not precisely, with one hundred percent certainty be three-dimensionally retrieved or reconstructed from the angiographic images alone. The missing 3D geometric features may, for example, include a diameter of a branch or vessel segment branching off from a vessel that contains a stenosis. Since the branched-off segment or vessel is typically not of any interest for characterizing the stenosis itself, the field of view and/or angulation of the angiographic images is typically not configured to acquire sufficient data to enable the complete 3D representation of the branched-of segment or vessel.

In a further act of the presently described method, the haemodynamic parameter is then assessed based on the generated complete set of 3D geometric features. This may, in other words, include a feature-based assessment or evaluation of the haemodynamic parameter.

In summary, one or more of the present embodiments are focused on cases in which the anatomical structure in the region of interest may only be partially represented or reconstructed (e.g., into one or more partial 3D representations that are not connected to each other), or cases in which it is not possible for any other reason to create a complete 3D model based on the angiographic images alone. This may, for example, be the case for a long, curved vessel segment with multiple stenoses, a complex bifurcation, a complex overlap between different vessels or parts of the vessel tree in the region of interest, or any combination of the above. One or more of the present embodiments may provide or define the complete set of geometric features or geometric information for the entire region of interest that is required for the haemodynamic assessment.

An accuracy of this assessment or prediction of the haemodynamic parameter may critically depend on an accuracy of the corresponding geometric features or geometry representation or description. For example, a predicted flow or flow feature may be significantly impacted by a geometry of stenosed segments as well as by a topology of the vessel tree, such as a presence, location, and/or size of side branches. This reflects the fundamental mechanism of flow distribution in a vessel tree, such as, for example, a coronary arterial tree. A functional significance of a vessel feature, such as a stenosis or a lesion, may be determined by a severity of ischaemia induced in a myocardial territory produced by the respective affected or hosting vessel. This may depend on the flowrate through the stenosis (e.g., the size of the myocardial supply area and a resistance to the flow posed by the stenosis). The geometry of the stenosis directly determines the resistance to flow exerted by the diseased arterial or other vessel segment. Arterial or other vessel trees or sub-trees containing one or more stenoses offer increased resistance to a flow, which causes a reduction in perfusion as compared to healthy conditions. In the case of multiple serially arranged diseased segments, this may make it difficult to evaluate the severity of each stenosis or lesion independently. It is, in other words, difficult to predict a priori whether, after revascularization of an upstream stenosis, a downstream stenosis will have a medically significant impact and therefore require further revascularization. In fact, by even partially restoring perfusion in the vessel tree or sub-tree through treatment of the upstream stenosis, an effective flowrate through the downstream stenoses may increase, which may correspondingly cause the medical significance of any downstream stenoses to also increase.

For each part of the region of interest (e.g., for each segment of the vessel tree), the angiographic images may provide different levels of detail and three-dimensional data. Accordingly, different views that indicate the level of available data or information may be defined. A complete view of a certain part allows for a complete representation of a 3D model of the part. A partial view only allows for a partial 3D representation of the part (e.g., for a 3D representation of a sub-part or sub-segment of the part). An incomplete view does not allow any 3D representation. An incomplete view may, however, allow for an extraction of a 2D geometric feature or 2D geometry information for or of the corresponding part of the region of interest or the corresponding vessel tree or vascular structure.

From complete or partial views, geometric features may be extracted after the respective 3D representation or reconstruction, while the missing geometric features may be estimated, for example, by making suitable assumptions. The partial extracted geometric features and the estimated geometric features may then be combined to recover or generate the complete geometric feature description of the region or vessel tree of interest. Even if a certain part or segment of the region of interest may not be three-dimensionally represented, an incomplete view, such as a single 2D angiographic image, of this part or segment may be available. In a development, at least one 2D geometric feature may therefore be extracted as the at least one additional geometric feature (e.g., from the incomplete view or single angiographic image). Geometric information contained in such incomplete views or single angiographic images, such as, for example, a width or a length, and/or a 2D shape of a vessel segment, may, in conventional reconstruction methods, be discarded. The present embodiments therefore make more efficient use of all available data than conventional methods, and may therefore provide an accurate assessment of the haemodynamic parameter while advantageously avoiding additional strain or exposure of the patient.

In a further development, the width of a vessel in at least one location in the region of interest is extracted as the additional geometric feature. This may, for example, be a two-dimensional width indicating or representing a diameter of the vessel in at least one spatial direction or dimension. As part of estimating the missing 3D geometric features, a constant diameter based on the width is then assumed for a segment of the vessel extending in the second portion of the region of interest. This provides that a regular tubular or cylindrical shape of the vessel may be assumed, while the diameter itself is derived or extracted from the available data (e.g., at least one of the angiographic images). Even healthy vessels or vessel segments and corresponding geometry or geometric features not immediately neighboring a steno sis may affect or be relevant for the haemodynamic parameter by influencing flow rates and/or pressure levels. Gaining the complete set of 3D geometric features by estimating the missing geometric features or missing geometric information may therefore lead to a more accurate assessment of the haemodynamic parameter as compared to an assessment based on an incomplete geometric characterization or description of the region of interest. Even if the estimated geometric features do not provide a perfectly accurate description of reality, the advantage gained by using the estimated geometric features or values may outweigh an alternative such as basing the assessment on an incomplete geometry or exposing the patient to additional radiation or medical procedures.

Effectively, the assumed tubular or cylindrical vessel segment having the measured diameter or radius may be stitched to the 3D reconstruction or 3D model of at least the first portion to generate or acquire the complete geometric characterization or description of the region of interest. The width (e.g., the diameter or radius) of the vessel may be extracted (e.g., may be measured) manually or automatically (e.g., by an image processing algorithm or image processing system). It may be advantageous to extract or measure the width of the vessel at different locations and to model the 3D geometry of the corresponding vessel or vessel segment based on these multiple extracted or measured widths to estimate the corresponding missing 3D geometric feature or features.

In an advantageous development, estimating the missing 3D geometric features includes assuming a longitudinally tapered or tapering shape for a segment of a vessel extending in the second portion (e.g., for a healthy segment leading to or away from a stenosis or lesion). This provides that the diameter of the segment that may not be estimated or reconstructed from the angiographic images on their own is assumed to increase or decrease along the longitudinal axis of the vessel segment. The longitudinal direction or axis corresponds to or is equal to a direction of flow through the segment or vessel.

To simplify any involved calculations as well as the assessment of the haemodynamic parameter, the diameter of the assumed or estimated tapered shape may increase or decrease, for example, linearly. The tapered shape or diameter of the segment may allow for the segment to be continuously combined with or stitched to different parts of the first portion (e.g., to different parts of the 3D representation without any discontinuities). This may result in an easy to calculate or easy to model characteristic or behavior of the vessel tree and, in turn, of the haemodynamic parameter. In other words, to estimate the missing 3D geometric features, it may be assumed that the segment, which may, for example, be a healthy segment connecting to serial stenoses or lesions, has a radius tapering or diameter tapering in accordance with a predefined spatial pattern or specification.

The above-mentioned linear change of the diameter is only one of multiple different possibilities. It may, for example, be possible to instead assume a quadratic relation. It may also be possible to extract or measure the width of the segment at multiple locations and derive the relation or dependence for the tapering of the diameter through an interpolation or a linear regression based on the multiple extracted or measured widths.

In a development, a geometric feature extracted from the 3D representation at a boundary between the first portion and the second portion is used as a constraint or boundary condition for estimating at least one missing 3D geometric feature for the second portion. It may, in other words, be estimated or assumed that even though the three-dimensional geometry or shape of a vessel segment in the second portion at or near the boundary to the first portion may not be represented or reconstructed, the vessel segment is connected to the first portion in a continuous manner (e.g., without discontinuities). This provides that for estimating the missing 3D geometric feature, extracted geometric features from the first portion and/or from the second portion may be used. Since the 3D geometric feature, such as, for example, a shape and/or diameter of a vessel segment, is precisely known in three dimensions, the correspondingly estimated missing 3D geometric feature may closely match reality. In turn, a precise and realistic assessment of the haemodynamic parameter may be achieved.

In a typical scenario for an application of this method, two spatially separated stenoses or lesions may be present in the region of interest. If a distance between these two stenoses or lesions is sufficiently large, then a healthy vessel segment connecting the two stenosed locations may be outside a field of view of the respective angiographic images taken to three-dimensionally image the two different diseased locations or segments. In this case, a 3D representation of the connecting healthy segment may therefore not be possible from the angiographic images alone. A shape of the connecting healthy segment or corresponding 3D geometric features may therefore be estimated by using the size and/or shape of corresponding vessel segments in the three-dimensionally represented parts containing the two diseased segments that are a respective continuation of the healthy segment.

Between the two boundaries, a smooth and continuous shape of the connecting healthy segment may be assumed. This may be a regularly shaped cylinder or tube if the shapes and sizes of the continuing three-dimensionally reconstructed vessel segments are equal to each other. If, however, one of the three-dimensionally reconstructed vessel segments has a different shape and/or size at the corresponding boundary than the other three-dimensionally reconstructed vessel segment at the other boundary (e.g., at the other end of the connecting healthy segment), then a smoothly tapered shape may be assumed or estimated for the connecting healthy segment, so that the segment may be stitched to the three dimensionally reconstructed segments at both ends or boundaries without discontinuities. This scenario corresponds to an advantageous development of the present embodiments, where the first portion and therefore the 3D reconstruction include at least two unconnected parts separated by the second portion. For estimating the missing 3D geometric features, a continuity (e.g., a continuous continuation) between the two parts is assumed for a vessel segment extending through the second portion and connecting the two unconnected parts of the first portion.

In a development, if a part of the second portion is visible in multiple of the angiographic images, all of these multiple angiographic images are taken into account in extracting and/or estimating a geometric feature of that part. For example, this may be done using a least-squares approximation of all corresponding data, geometric features, or values thereof derived from the multiple angiographic images for that part. Even if the part of the second portion, (e.g., a certain vessel segment) may not be three-dimensionally represented completely from the angiographic images, the part of the second portion may be pictured multiple times in different of the angiographic images. Extracting a geometric feature, such as, for example, a width of the vessel segment from the multiple angiographic images independently may then result in multiple different values of or for that specific geometric feature. In this case, all of these multiple values or data from the multiple angiographic images or multiple views of the part may then be reconciled to arrive at a final value defining the geometric feature to be used in assessing the haemodynamic parameter. In this way too, all available data is used to achieve the best possible (e.g., the most accurate or realistic) assessment of the haemodynamic parameter.

The different values for the same geometric feature resulting from different angiographic images of the same part may, for example, result from differences in angulation and/or image quality. If, for example, two of the multiple angiographic images have been taken using different focal planes or focal lengths, then a geometric feature, such as a width or diameter of a vessel, derived from each of these multiple angiographic images may differ from the others, for example, if the vessel segment is out of focus in one or both of the angiographic images. It may also be possible that a width or diameter of the vessel derived from different angiographic images may differ due to a perspective distortion. This may, for example, be the case if the vessel is imaged from different angles and has a shape or cross-section differing from a perfect circle.

In a development, if the region of interest includes multiple stenosed vessel segments in unconnected parts of the first portion, the missing 3D geometric features are estimated in dependence on a hierarchy (e.g., a user-defined hierarchy or hierarchy scheme) for connecting the stenosed vessel segments. In other words, a hierarchy scheme or topology that defines an order or a spatial relation in which the stenosed vessel segments are to be arranged or connected to each other to match reality. Especially in complex geometries, where multiple vessels or branches of the vessel tree may overlap each other or criss-cross in front of each other, it may be difficult to automatically determine the topology of the vessel tree (e.g., which of the stenosed vessel segments is directly or indirectly connected to which of the other stenosed vessel segments). The hierarchy or hierarchical scheme may provide that the complete set of 3D geometry features accurately describes the real topology of the vessel tree. This topology is of particular importance for assessing the haemodynamic parameter, because there may be a significant degree of interdependence between vascular branches on flow patterns or circulation.

In a development, if the region of interest contains multiple stenoses (e.g., located in different branches of a vessel tree), their relative positions with respect to each other are taken into account in assessing the haemodynamic parameter. This provides that the interdependence between different segments or branches of the vessel tree with regards to a flow or circulation in the vessel tree and the corresponding effect on the haemodynamic parameter is reflected in the assessment. Whereas for characterizing a geometry of each stenosis, only an immediate location or surroundings of the respective stenosis are relevant and are therefore imaged in typical angiography, this is not the case for assessing the haemodynamic parameter for a larger region of interest, such as a vessel tree or sub-tree including multiple vessels and/or bifurcations or branches. It may, for example, be possible that one stenosis may influence the haemodynamic parameter on a scale or at a distance from that stenosis that is larger than a field of view or area of focus of a typical angiographic image. By taking into account the relative positions of the multiple stenoses in the region of interest, the accuracy of the assessment of the haemodynamic parameter may therefore be improved.

In a development, the angiographic images are acquired using at least two different medical imaging modalities. Generating the complete set of 3D geometric features and in turn the assessment of the haemodynamic parameter may, in other words, be based on different types of images or image data. Different imaging modalities or imaging techniques may, for example, include x-ray imaging, computed tomography (CT), coronary computed tomography angiography (CCTA), magnetic resonance imaging (MRI), micro-angiography, peripheral angiography, and/or others. Using different imaging modalities may result in a more accurate geometric description or characterization of the region of interest and therefore in an improved accuracy of the assessment of the haemodynamic parameter. This may be the case because different imaging modalities may provide different image qualities, contrast ratios, sharpness value, for example, for borders between different anatomical features or tissues, and the like. This provides that different geometric features may be extractable from different types of images with different degrees of accuracy or certainty.

The geometric features may be extracted from different images or data sets independently of each other and/or independently of what imaging modality or technique has been used, while still being able to be combined to generate the complete set of 3D geometric features to fully geometrically characterize the region of interest. Therefore, the haemodynamic parameter may be assessed with particular accuracy even in cases where, for example, images acquired through different imaging modalities or techniques may not, may not reliably, or may only with unreasonable effort be combined into a single 3D representation. For example, CCTA may provide vessel centerlines and an approximation of geometric features of a vessel, such as radius or diameter and/or a length. These geometric features may then be combined with data extracted from or based on other types of images, which may, for example, provide a more accurate characterization of a large-scale topology or any other useful characteristic compared to the CCTA data.

In a development, a confidence value or confidence measure is calculated or computed for at least one of the geometric features and/or for the assessment of the haemodynamic parameter. The confidence value may, in other words, be determined for any or all of the extracted and/or estimated geometric features and/or for the complete set of geometric features and/or for the assessment or a final result thereof. The confidence value or confidence measure may quantify an uncertainty in the respective quantities or values (e.g., in the respective geometric features, corresponding values or sizes and/or the assessment itself). The confidence value may describe the level of confidence in the computed quantities or values and/or a respective sensitivity to complete or incomplete features (e.g., to extracted or estimated geometric features). Calculating and providing the confidence value may be of particular advantage for the present embodiments, since it does rely on certain estimations or assumptions. If, for example, a larger portion of the complete set of 3D geometric features has been estimated as opposed to having been directly extracted from the 3D representation, then a correspondingly lower confidence value may be assigned to or associated with the resulting assessment of the haemodynamic parameter. The confidence value may help or assist medical personnel in deciding if additional images of the patient may be acquired. The confidence value may, in other words, advantageously result in an optimal trade-off between an accuracy of the assessment of the haemodynamic parameter and a strain or exposure of the patient.

Confidence values may be calculated for values of a certain geometric feature that has independently been extracted multiple times from multiple different angiographic images. Correspondingly, a weighting function may be used for selecting and combining geometric features or values thereof from different views and/or from different ones of the angiographic images. The geometric features may, in other words, be combined such that respective confidence values or the respective confidence values of the views or angiographic images from which the geometric features are derived are reflected in a representation in or an influence on the complete set of 3D geometric features and/or the assessment of the haemodynamic parameter. This enables the use of all available data, while identifying an influence of outliers.

In a further development, the confidence value is calculated based on an image quality metric of at least one of the angiographic images from which the geometric feature and/or the assessment is derived. The confidence value may, in other words, be calculated or computed as a function of the image quality of the angiographic images. Lower image quality of a particular angiographic image or view can result in a lower confidence value of any values, features, or characteristics derived therefrom. The image quality or the image quality metric may, for example, be determined by a resolution, a sharpness, a contrast ratio, or the like.

Multiple image quality values may be determined for different regions or parts of any single angiographic image or view. If, for example, only one vessel segment centrally located in an angiographic image is in focus (e.g., is imaged sharply), a relatively high confidence value may be assigned to a geometric feature derived or extracted from that particular, central vessel segment. At the same time, another geometric feature may be extracted from a different part of the same angiographic image, for example, for a neighboring healthy vessel segment that is out of focus. Since oftentimes in angiographic imaging no particular attention is paid to an image quality for vessels or segments other than those containing or immediately surrounding a stenosis or lesion of interest, determining and using an image quality metric with sub-image level accuracy may be particularly advantageous for the presently described method. This may be the case because it may ultimately result in a more accurate assessment of the haemodynamic parameter and/or a more accurate confidence value of the assessment.

In a further development, based on the provided angiographic images, it is automatically determined or computed what additional input data could or would improve the calculated confidence value. A corresponding suggestion is then issued. If, for example, a specific geometric feature has a confidence value below a predetermined threshold, then it may be suggested to acquire an additional angiographic image of a specific part of the region of interest corresponding to that geometric feature. This may limit the number of additional images that are to be acquired to achieve an assessment of the haemodynamic parameter with at least a minimum confidence value. Therefore, any additional strain or exposure for the patient may be minimized. The suggestion may also contain or provide specific parameters for a suggested image acquisition, such as a specific or minimal dosage of a contrast agent and/or a specific angulation and/or an imaging modality to be used. The suggestion may be issued automatically or only if a confidence value of the assessment of the haemodynamic parameter, or of one or more geometric features is below a predefined threshold. It may be possible for medical personnel to request a suggestion at any time, regardless.

In a development, at least some of the geometric features (e.g., the complete set of 3D geometric features) are provided as an input or input vector to a computing system that has been correspondingly trained through use of a machine learning method for assessing the haemodynamic parameter. The computing system may, for example, be or include an artificial neural net. The computing system may also be denoted as a machine learning predictor, since assessing the haemodynamic parameter may include predicting a corresponding value such as, for example, a fractional flow reserve (FFR). The FFR is defined as the blood pressure after or distal to a stenosis relative to the pressure before or upstream of the stenosis. Typically, multiple features may be employed for multiple stenoses, where the stenoses may be ordered based on severity. In this case, for a healthy region or segment, only a length and a radius or diameter may be used as input. Since the geometric features of the stenosed segments may be the most influential (e.g., the most important) for assessing the haemodynamic parameter, the computing system may be focused on these features by limiting the geometric features of healthy segments in the input vector. When using the computational system based on machine learning, the input vector may, in other words, be derived from or include a set of measurements performed on the angiographic images. In this case, an explicit representation of the region of interest or the vessel tree of interest (e.g., a fully reconstructed 3D model) may not be needed, as long as the input vector contains the required geometric features.

In general, several different computational models may be adopted to predict functional indices from geometric features or, in terms of the present embodiments, to assess the haemodynamic parameter. In one embodiment, the computational model may be a fluid dynamics model describing blood flow inside an arterial tree. In this case, an explicit representation of the arterial tree typically is to be extracted or generated from the respective provided medical imaging data (e.g., the angiographic images).

Another aspect is a system for assessing the haemodynamic parameter for the vascular region of interest of a patient based on angiographic images. The system includes a processing unit (e.g., a processor), a data storage unit (e.g., a memory) connected thereto and containing a program code, and an input-output-subsystem. The program code is executable by the processing unit, providing that the processing unit is designed or configured to be executed by the processing unit. The program code may encode or represent the acts of a method according to the present embodiments. The system is configured to execute the program code to process the angiographic images provided to the system via the input-output-subsystem and to output a resulting assessment of the haemodynamic parameter. The system is, in other words, configured to execute at least one embodiment of the method. The input-output-subsystem can include one or more interfaces. The system may also include a display unit for displaying, for example, the computed assessment of the haemodynamic parameter, the angiographic images, the 3D reconstruction, the extracted and/or estimated geometric features, and/or the suggestion. The system may also include the computing system (e.g., the artificial neural net).

The embodiments and developments described herein for at least one aspect (e.g., for the method and the system), as well as the corresponding advantages may be applied to any and all aspects of the present embodiments.

BRIEF DESCRIPTION OF THE DRAWINGS

The features and feature combinations previously mentioned in the description as well as the features and feature combinations mentioned in the following description and/or shown in the figures alone may be employed not only in the respectively indicated combination but also in other combinations or taken alone without leaving the scope of the present invention.

DETAILED DESCRIPTION

Figure 1:
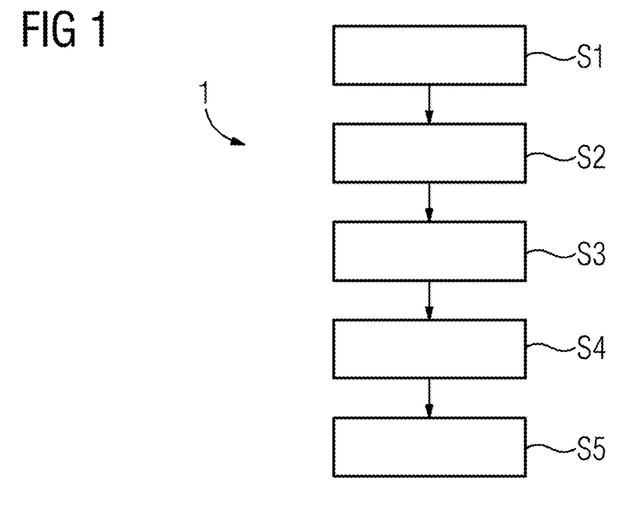
FIG. 1 schematically shows a flow chart for one embodiment of a method for assessing a haemodynamic parameter for a region of interest based on angiographic images.

FIG. 1 schematically shows a flow chart 1 of one embodiment of a method for assessing a haemodynamic parameter such as a fractional flow reserve (FFR) based on multiple angiographic images. In a process act S1, the angiographic images of a vascular region of interest are acquired. This may include actually taking the images using a medical imaging system or device and/or may include accessing a data storage device on which the angiographic images are stored. The region of interest may contain or include multiple different sub-regions, parts, or portions. The angiographic images may contain or enable one or more complete, partial, or incomplete views of each of these parts or portions.

In a process act S2, a 3D representation or reconstruction of at least a first portion of the region of interest is obtained based on the angiographic images. Geometric features are extracted from complete or partial views of a respective anatomical structure of interest (e.g., from the 3D representation). The region of interest or the anatomical structure of interest may, for example, be a vascular tree or a sub-tree that may be a part of the vascular tree.

In a process act S3, additional geometric features of the anatomical structure are extracted from partial incomplete views, which only allow the extraction of 2D geometry information (e.g., geometric features) for a corresponding part of the anatomical structure.

In a process act S4, a complete set of 3D geometric features of the anatomical structure are generated or defined by combining the extracted geometric features from the complete or partial views as well as from the partial incomplete views, and by using appropriate estimations or assumptions for the missing 3D geometric features. From complete or partial views, geometric features may be extracted after a respective 3D representation or reconstruction, and missing geometric features may be estimated (e.g., by making suitable assumptions regarding the missing information or geometry). The partial geometric features may then be combined to recover the most complete feature description of the anatomical structure of interest possible. In case additional data or information is available from incomplete views, partial incomplete geometric features may be extracted, and the incomplete views may be completed by appropriate estimations or assumptions. By combining the complete and incomplete partial features, the resulting combined geometric feature set may represent the anatomical or vascular structure of interest more accurately. Complete partial and incomplete partial geometric feature descriptions may also be generically combined. A respective confidence value may, for example, also be calculated for one or more of the geometric features.

In a process act S5, an assessment of the haemodynamic parameter (e.g., the FFR) is performed based on the complete set of geometric features (e.g., based on the complete feature description of a coronary segment or vessel tree). A confidence value for the assessment may also be calculated. A suggestion based on one or more of the calculated confidence values may also be generated and provided.

Exemplary details and applications of this method or individual process acts thereof are explained below with reference to FIGS. 2 to 6.

Figure 2:
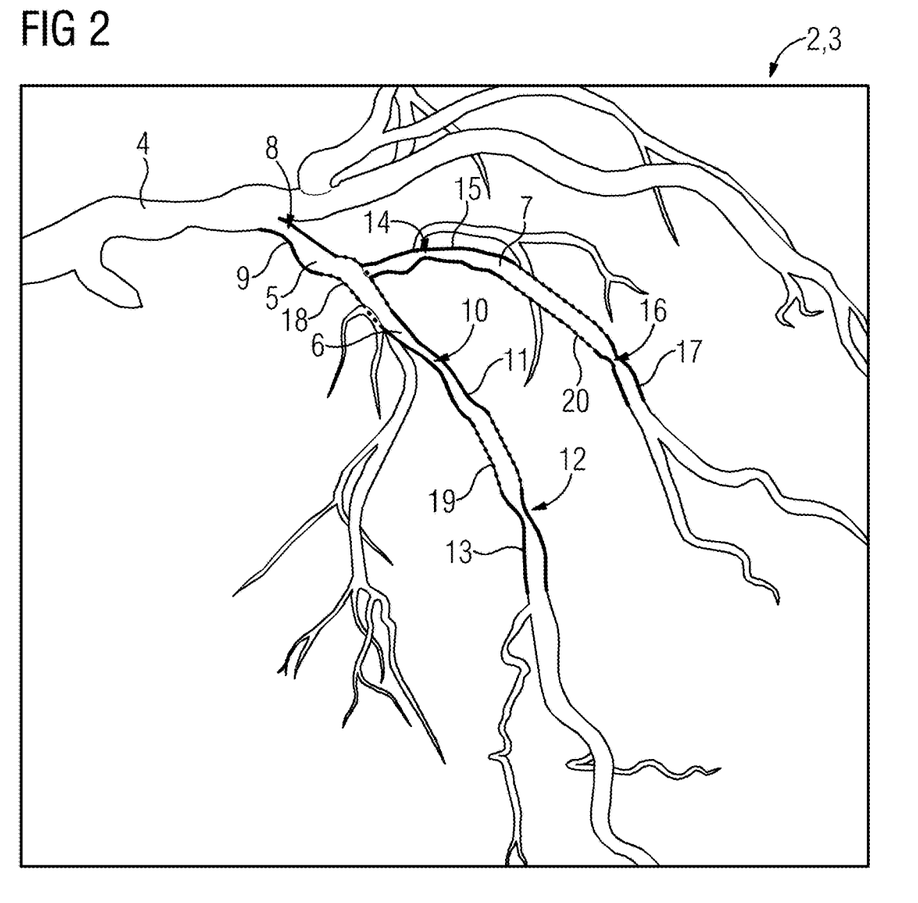
FIG. 2 schematically shows a first exemplary angiogram of a first vascular region of interest containing multiple stenoses.

FIG. 2 schematically shows a first angiogram 2 of a first vascular region of interest 3. Therein, a first vessel tree 4 of a patient is shown. Of particular interest in this example is a sub-tree of the first vessel tree 4. The sub-tee includes a parent branch 5, a first daughter branch 6, and a second daughter branch 7.

A case in which multiple stenoses may be identified in one or more vascular branches of the first vessel tree 4 in one or more angiographic images or views is considered. A 3D representation of the complete first vessel tree 4 or even of the complete sub-tree may not be possible, because not all the parts or segments of all vascular branches or vessels (e.g., of the branches 5, 6, 7) are visible in at least two angiographic views or images with different angulations. Instead, a number of 3D representations of different parts or segments for which at least a pair of suitable angiographic views is available may be performed. 3D geometric features of these three-dimensionally represented or reconstructed parts or segments may then be extracted. To acquire a complete set of geometric features for the first vessel tree 4 or the sub-tree, the missing geometric features or geometry information may be estimated and combined with the extracted geometric features.

In the first angiogram 2, a first stenoses 8 is visible in a first segment 9 of the parent branch 5. Additionally, a second stenosis 10 is visible in a second segment 11 of the first daughter branch 6. A third stenoses 12 is visible in a third segment 13 of the first daughter branch 6. A fourth stenoses 14 is visible in a fourth segment of the second daughter branch 7. A fifth stenoses 16 is visible in a fifth segment 17 of the second daughter branch 7. The segments 9, 11, 13, 15, 17 each containing one of the multiple stenoses 9, 10, 12, 14, 16 have, in this example, been fully imaged and may therefore be segmented and three-dimensionally represented. These segments 9, 11, 13, 15, 17 may therefore form or be considered to be a first portion of the first region of interest 3. This provides that in this example, the first portion includes multiple unconnected three-dimensionally represented parts.

The three-dimensionally represented or representable parts being unconnected provides that between any two of these parts there is a part or segment that may not be fully three-dimensionally represented based on the data or information contained in the first angiogram 2 and/or additional available angiographic images. Between the first segment 9, the second segment 11, and the fourth segment 15, there is a first connecting segment 18. Between the second segment 11 and the third segment 13, there is a second connecting segment 19. Between the fourth segment 15 and the fifth segment 17, there is a third connecting segment 20. These connecting segments 18, 19, 20 are healthy vascular segments that have not been sufficiently imaged to allow a complete and accurate 3D representation. This may, for example, be the case because of overlap with other anatomical structures that may obfuscate the connecting segments 18, 19, 20. A user may also simply choose to not represent in 3D the connecting segments 18, 19, 22 to reduce processing time. Since the connecting segments 18, 19, 20 may not be represented in 3D, the connecting segments 18, 19, 20 may form or be considered to be a second portion of the first region of interest 2.

To nevertheless acquire a complete geometric description or geometric feature set for the sub-tree, multiple scenarios or approaches may be envisioned. For example, a width of one or more of the connecting segments 18, 19, 20 representing a respective diameter or radius may be manually or automatically measured at one or more locations between the diseased segments 9, 11, 13, 15, 17. The diameter or radius may then be assumed to be constant for the entire respective connecting segment 18, 19, 20.

In another example, the assumption may be made that one or more of the connecting segments 18, 19, 20 connecting at least two of the serial stenoses 8, 10, 12, 14, 16 has a tapered or conical shape with a radius or diameter tapering along the length of the respective connecting segment 18, 19, 20 according to a predefined spatial pattern.

In another example, one or more of the connecting segments 18, 19, 20 may be clearly visible in one view, while only a centerline of the respective vessel or connecting segment 18, 19, 20 may be identified in a second view or angiographic image. The centerline may be three-dimensionally reconstructable, while for a complete 3D representation of the respective connecting segment 18, 19, 20, the radius or diameter may be derived from a width of the respective connecting segment 18, 19, 20 in or extracted from a single view or angiographic image.

In yet another example, one or more of the connecting segments 18, 19, 20 are clearly visible in one view, while no additional information or geometric features may be identified or extracted from a second view. The respective connecting segment 18, 19, 20 may then be geometrically characterized by a radius or diameter and a length as extracted from the one single view in which the length is clearly visible.

Figure 3:
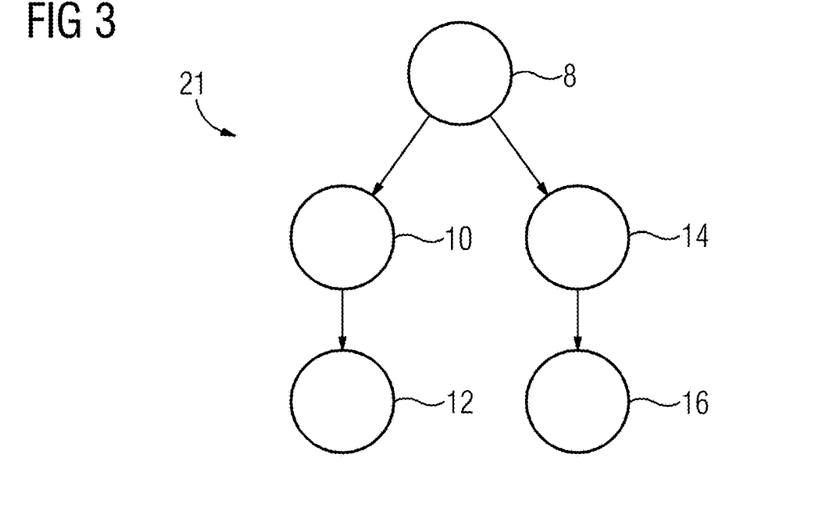
FIG. 3 schematically shows an exemplary hierarchy scheme for connecting the multiple stenoses shown in FIG. 2.

Since only the diseased segments 9, 11, 13, 15, 17 are or may be segmented, a user may specify or provide a hierarchy scheme 21 as schematically shown in FIG. 3. This may typically be useful in case a coronary tree, such as the first vessel tree 4, has multiple stenoses 8, 10, 12, 14, 16 and the user wants to minimize segmentation requirements. The healthy connecting segments 18, 19, 20 do not require a segmentation, since the diameter of the healthy connecting segments 18, 19, 20 may be estimated from the respective bordering bottom or top diameter of the respective neighboring segmented segments 9, 11, 13, 15, 17. If, for example, a fluid dynamics model is employed for modeling a blood flow in the first vessel tree 4 or a respective haemodynamic parameter, the anatomical models or 3D representations of the stenoses 8, 10, 12, 14, 16 or the respective surrounding diseased segments 9, 11, 13, 15, 17 may be connected by generating respective cylindrical or tapering tubes representing the connecting segments 18, 19, 20 that are stitched to the respective neighboring diseased segments 9, 11, 13, 15, 17.

The hierarchy scheme 21 provides a reference for the topology of the first region of interest 3 or, in this case of the sub-tree consisting of the parent branch 5, the first daughter branch 6, and the second daughter branch 7. The hierarchy scheme 21, in other words, specifies a spatial relation between the diseased segments 9, 11, 13, 15, 17 (e.g., how the diseased segments 9, 11, 13, 15, 17 are or should be connected). The hierarchy scheme 21 may, for example, be referenced by or used as an additional input for an algorithm or computing system.

With regards to bifurcations geometries or geometric features, two branches of a bifurcation (e.g., LAD and LCx) may be separately represented in 3D, each one based on two separate views. The corresponding third branch (e.g., LM) may be visible in some partial views. In this example, geometric features may be extracted from the 3D representations of the first two branches, each showing an individual branch and/or stenosis. For the third branch, geometric features may be estimated to get a complete geometric feature description for the bifurcation. This complete geometric feature set is then used for the haemodynamic assessment (e.g., for assessing the haemodynamic parameter). For estimating the geometric features for the third branch, a radius or diameter value may be estimated from a partial view. The assumption may then be made that the third branch is healthy and a diameter of the third branch is equal to the estimated or measured diameter value. If a 3D reconstruction of the complete bifurcation is required for the haemodynamic assessment or analysis, the third branch may be represented by a cylinder with a circular cross-section with a radius or diameter equal to the estimated or measured respective value.

Figure 4:
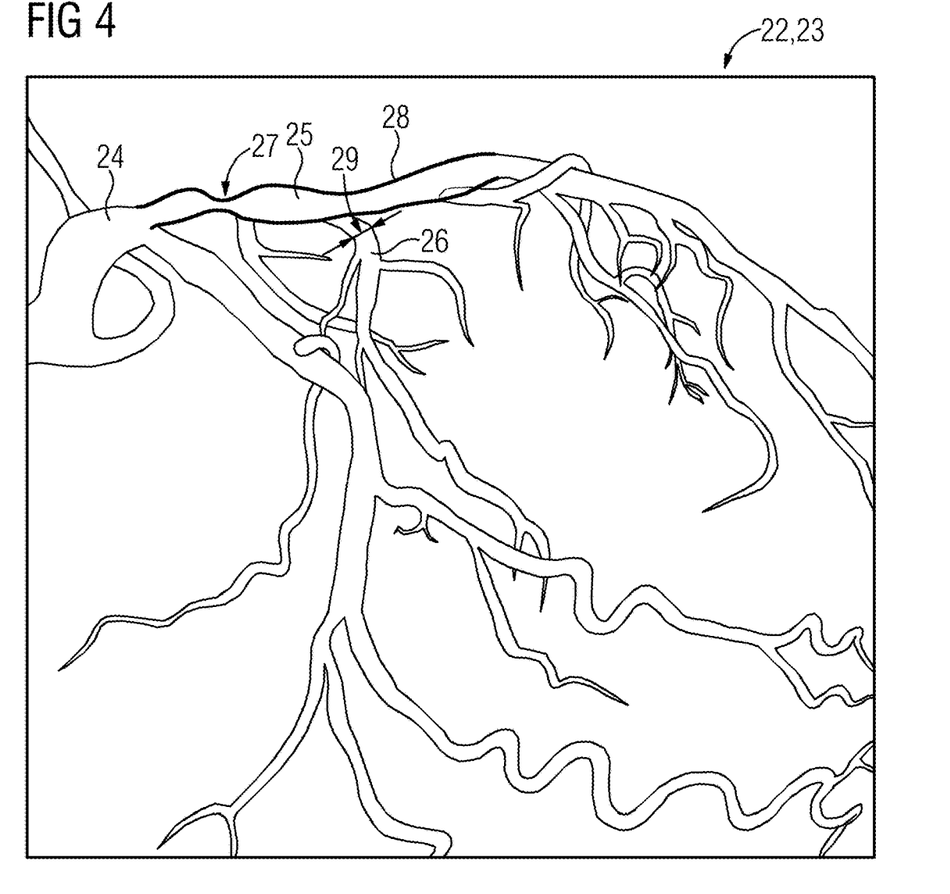
FIG. 4 schematically shows a second exemplary angiogram of a second vascular region of interest containing a stenosis.

FIG. 4 schematically shows a second angiogram 22 for a second vascular region of interest 23. Therein, a second vessel tree 24 is shown. The second vessel tree 24 includes a main branch 25 and a side branch 26 that branches off from the main branch 25. Presently, the main branch 25 contains a stenoses 27 in a fully segmented and therefore three-dimensionally representable or reconstructable vessel segment 28. The side branch 26 is healthy, providing that the side branch 26 does not contain a stenosis or lesion.

Even though the side branch 26 branches off from the main branch 25 at a downstream location with respect to the stenosis 27, the side branch 26 or a geometry or geometric features of the side branch 26 may still be important for evaluating the upstream stenosis 27 or assessing a corresponding haemodynamic parameter. A coronary bed supplied by the healthy side branch 26 demands a certain amount of oxygen and blood, and, as a result, a blood flow through the stenosis 27 is increased. However, since the side branch 26 is healthy, a segmentation is not required, providing that the side branch 26 is not sufficiently imaged during the corresponding angiography and may therefore not be three-dimensionally represented or reconstructed. A width of the side branch 26 may be manually or automatically measured or extracted as a geometric feature of the side branch 26 (e.g., at a measuring location 29). A diameter of the side branch 26 may be derived or estimated from the measured width. The estimated diameter may suffice for in turn estimating an influence of the side branch 26 on the upstream stenosis 27 and/or the corresponding assessed haemodynamic parameter or functional index of interest.

In case a machine learning predictor, such as a trained artificial neural net, is used in the assessment of the functional haemodynamic parameter, the measured or extracted diameter of the side branch 26 and/or one or more similar or corresponding values may be used directly as an input or as part of an input vector for the machine learning predictor or artificial neural net. If multiple such values or geometric features are used, values or the geometric features may be ordered by respective values (e.g., by the values or sizes of the diameters of different segments or side branches or measuring locations). This may reflect or take into account a typical structure of a vascular tree, where a diameter of segments or side branches typically decreases in a downstream direction. In this case, the stitching of multiple segments, branches, or vessels may simply be reflected by the introduction of additional geometric features or corresponding values, for example, to the machine learning predictor or the input vector.

Figure 5:
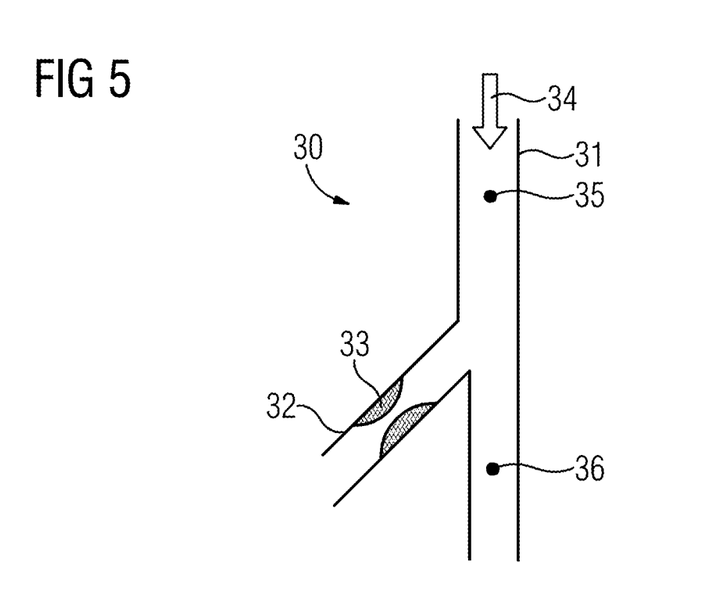
FIG. 5 schematically shows a first exemplary vessel sub-tree with a stenosis in a diseased side branch.
Figure 6:
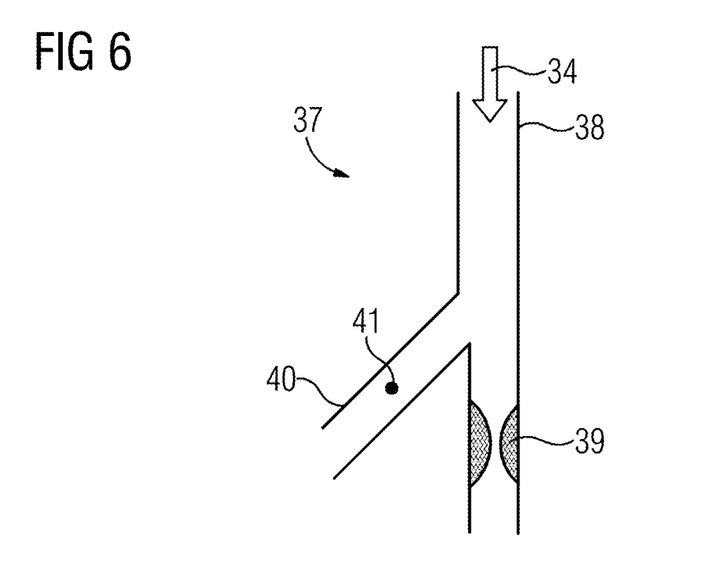
FIG. 6 schematically shows a second exemplary vessel sub-tree with a stenosis in a diseased main branch.

For understanding coronary circulation and correctly assessing a corresponding haemodynamic parameter, there may be a significant degree of interdependence between different vascular branches. Referring now to FIGS. 5 and 6, two examples are discussed below. For the sake of simplicity and with natural generalization to more complex cases being possible, both examples include a simple bifurcation that may be seen as a sub-tree of a larger and more complex vascular tree. When assessing a haemodynamic parameter, the presence of a stenosis in one part or segment of the bifurcation or sub-tree may lead to an increased flow resistance and therefore to a decreased flow in the entire sub-tree.

FIG. 5 schematically shows a first sub-tree 30 including a healthy main branch 31 and a diseased side branch 32 containing a stenosis 33. An arrow schematically indicates a direction of flow 34 through the first sub-tree 30. For this example, a first observation point 35 and a second observation point 36 both located in the healthy main branch 31 are considered. The first observation point 35 is located upstream of the diseased side branch 32, while the second observation point 36 is located downstream of the diseased side branch 32 (e.g., downstream of the bifurcation). The fluid dynamics or haemodynamics at both observation points 35, 36 are influenced by the stenosis 33 in the diseased side branch 32. In fact, a pressure drop between the first observation point 35 and the second observation point 36 is decreased compared to a situation without the stenosis 33, because of a reduction in blood flow due to the presence of the stenosis 33. Under the assumption that a blood pressure at a root of the larger vascular or coronary tree (e.g., an aortic pressure) is not changed when moving from a healthy condition to the shown diseased condition of the first sub-tree 30, an absolute pressure in the segment of the healthy main branch 31 located downstream of a point or location where the diseased side branch 32 branches off is influenced.

Similarly to FIG. 5, FIG. 6 schematically shows a second sub-tree 37 including a diseased main branch 38 containing a stenosis 39, and a healthy side branch 40. A third observation point 41 located in the healthy segment 40 is considered. In this example, the presence of the stenosis 39, even though the stenosis 39 is located downstream of a branching-off-point of the healthy side branch 40, influences the fluid dynamics or haemodynamics at the third observation point 41 in the healthy side branch 40. The stenosis 39 leads to a lower or reduced flow and a lower pressure drop in the diseased main branch 38 upstream of the stenosis 39 (e.g., upstream of the healthy side branch 40). Thus, the stenosis 39 leads to a changed or different absolute pressure level even in the healthy side branch 40 as compared to a healthy situation without the stenosis 39.

These examples demonstrate the importance of a comprehensive characterization of a vascular or coronary tree, both in terms of geometry or geometric features and thus severity of each stenosis or lesion, and the topology of the vascular tree or network of vessels.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for assessing a haemodynamic parameter for a vascular region of interest of a patient based on angiographic images, the method comprising:
acquiring multiple angiographic images of the vascular region of interest, the multiple angiographic images showing at least a first portion of the vascular region of interest from at least two different angles to allow for a three dimensional (3D) representation of the first portion of the vascular region of interest;
generating the 3D representation of at least the first portion of the vascular region of interest from the multiple angiographic images;
extracting 3D geometric features of the first portion of the vascular region of interest from the 3D representation;
extracting at least one additional geometric feature for at least a second portion of the vascular region of interest from the multiple angiographic images, wherein the multiple angiographic images include insufficient data about the second portion of the vascular region of interest to allow for a complete 3D representation of the second portion of the vascular region of interest;
generating a complete set of 3D geometric features for the vascular region of interest, the generating of the complete set of 3D geometric features comprising combining the extracted 3D geometric features and the at least one additional geometric feature, and estimating any missing 3D geometric features from the extracted geometric features based on a predefined ruleset; and
assessing the haemodynamic parameter based on the generated complete set of 3D geometric features.

2. The method of claim 1, wherein at least one two-dimensional (2D) geometric feature is extracted as the at least one additional geometric feature.

3. The method of claim 1, wherein extracting at least one additional geometric feature comprises extracting a width of a vessel in at least one location in the vascular region of interest, and
wherein estimating any missing 3D geometric features comprises assuming a constant diameter based on the width for a segment of the vessel extending in the second portion.

4. The method of claim 1, wherein estimating any missing 3D geometric features comprises assuming a longitudinally tapered shape for a segment of a vessel extending in the second portion.

5. The method of claim 4, wherein the segment is a healthy segment leading to or away from a stenosis.

6. The method of claim 1, wherein a geometric feature extracted from the 3D representation at a boundary between the first portion and the second portion is used as a constraint for the estimating of at least one missing 3D geometric feature for the second portion.

7. The method of claim 1, wherein the first portion and, therefore, the 3D representation comprise at least two unconnected parts separated by the second portion, wherein estimating any missing 3D geometric features comprises assuming a continuity between the two unconnected parts for a vessel segment extending through the second portion and connecting the two unconnected parts of the first portion.

8. The method of claim 1, wherein when a part of the second portion is visible in multiple of the angiographic images, all of the multiple angiographic images are taken into account in extracting, estimating, or extracting and estimating a geometric feature of that part.

9. The method of claim 8, wherein when the part of the second portion is visible in the multiple angiographic images, all of the multiple angiographic images are taken into account in the extracting, the estimating, or the extracting and estimating of the geometric feature of that part using a least-squares approximation of all corresponding data derived from the multiple angiographic images.

10. The method of claim 1, wherein when the region of interest includes multiple stenosed vessel segments in unconnected parts of the first portion, the missing 3D geometric features are estimated in dependence on a hierarchy for connecting the stenosed vessel segments.

11. The method of claim 10, wherein the hierarchy is a user-defined hierarchy.

12. The method of claim 1, wherein when the vascular region of interest includes multiple stenoses, relative positions with respect to each other, respectively, are taken into account in assessing the haemodynamic parameter.

13. The method of claim 12, wherein when the vascular region of interest includes multiple stenoses located in different branches of a vessel tree, relative positions with respect to each other, respectively, are taken into account in assessing the haemodynamic parameter.

14. The method of claim 1, wherein acquiring the multiple angiographic images comprises acquiring the multiple angiographic images using at least two different medical imaging modalities.

15. The method of claim 1, further comprising calculating a confidence value for at least one of the geometric features, for the assessment of the haemodynamic parameter, or for a combination thereof.

16. The method of claim 15, wherein calculating the confidence value comprises calculating the confidence value based on an image quality metric of at least one of the angiographic images from which the at least one geometric feature, the assessment, or the at least one geometric feature and the assessment are derived.

17. The method of claim 16, further comprising:
automatically computing, based on the provided angiographic images, what additional input data could improve the calculated confidence value; and
issuing a corresponding suggestion.

18. The method of claim 1, wherein assessing the haemodynamic parameter comprises providing at least some of the geometric features as an input vector to a computing system that is correspondingly trained through a machine learning method.

19. The method of claim 18, wherein the at least some of the geometric features comprises the complete set of 3D geometric features, and
wherein the computing system comprises an artificial neural net.

20. A system for assessing a haemodynamic parameter for a vascular region of interest of a patient based on angiographic images, the system comprising:
a processor;
a data storage unit in communication with the processor, the data storage unit storing program code; and
an input-output-subsystem,
wherein the program code includes instructions that are executable by the processor to assess the haemodynamic parameter for the vascular region of interest of the patient based on the angiographic images, the instructions comprising:
identifying multiple angiographic images of the vascular region of interest, the multiple angiographic images showing at least a first portion of the vascular region of interest from at least two different angles to allow for a three dimensional (3D) representation of the first portion of the vascular region of interest;

generating the 3D representation of at least the first portion of the vascular region of interest from the multiple angiographic images;

extracting 3D geometric features of the first portion of the vascular region of interest from the 3D representation;

extracting at least one additional geometric feature for at least a second portion of the vascular region of interest from the angiographic images, wherein the angiographic images include insufficient data about the second portion of the vascular region of interest to allow for a complete 3D representation of the second portion of the vascular region of interest;

generating a complete set of 3D geometric features for the vascular region of interest, the generating of the complete set of 3D geometric features comprising combining the extracted 3D geometric features and the at least one additional geometric feature, and estimating any missing 3D geometric features from the extracted geometric features based on a predefined ruleset; and assessing the haemodynamic parameter based on the generated complete set of 3D geometric features, and wherein the multiple angiographic images are provided to the system via the input-output-subsystem, and the system is configured to output the assessment of the haemodynamic parameter.

\* \* \* \* \*